(12) United States Patent  (10) Patent No.: US 6,200,272 B1
Linden  (45) Date of Patent: Mar. 13, 2001

(54) FOLDING CARD DEVICE FOR EVALUATING PROTECTIVE SENSATION

(75) Inventor: Harry Linden, Santa Barbara, CA (US)

(73) Assignee: Curative Health Services, Inc., Hauppauge, NY (US)

( * ) Notice: Subject to any disclaimer, the term of this patent is extended or adjusted under 35 U.S.C. 154(b) by 0 days.

(21) Appl. No.: 09/327,688

(22) Filed: Jun. 8, 1999

(51) Int. Cl.[7] ....................................................... A61B 5/00
(52) U.S. Cl. ............................................................. 600/557
(58) Field of Search ................................... 600/552, 556, 600/557, 583; 132/321, 323, 328, 329

(56) References Cited

U.S. PATENT DOCUMENTS

| | | |
|---|---|---|
| D. 204,651 | 5/1966 | Laughlin . |
| D. 265,515 | 7/1982 | Levine . |
| D. 272,565 | 2/1984 | Levine . |
| D. 298,353 | 11/1988 | Manno . |
| 791,638 * | 6/1905 | Metzger ............................... 132/321 |
| 2,035,425 * | 3/1936 | Poll ...................................... 132/329 |
| 3,185,146 | 5/1965 | Leopoldi . |
| 3,662,744 | 5/1972 | Law et al. . |
| 3,933,148 | 1/1976 | Wyler et al. . |
| 4,877,037 | 10/1989 | Ko et al. . |
| 5,016,659 * | 5/1991 | Mas ...................................... 132/321 |
| 5,119,941 * | 6/1992 | Lepie ................................... 132/321 |
| 5,244,299 | 9/1993 | Chu . |
| 5,316,011 | 5/1994 | Weintein et al. . |
| 5,381,806 | 1/1995 | Weinstein et al. . |
| 5,445,163 | 8/1995 | Machacek . |
| 5,474,084 | 12/1995 | Cunniff . |
| 5,492,132 | 2/1996 | Weinstein et al. . |
| 5,529,074 | 6/1996 | Greenfield . |
| 5,666,963 | 9/1997 | Swenson et al. . |
| 5,673,706 | 10/1997 | Scott . |
| 5,810,743 | 9/1998 | Cronin . |
| 5,820,560 | 10/1998 | Sinderby et al. . |
| 5,823,969 | 10/1998 | Christy . |

* cited by examiner

*Primary Examiner*—Cary O'Connor
*Assistant Examiner*—Pamela Wingood
(74) *Attorney, Agent, or Firm*—Dorsey & Whitney LLP

(57) ABSTRACT

A device for evaluating protective sensation, comprising a probe and a folding card attached to the probe, such that a portion of the probe extends from the folding card when the folding card is in a first position. The device may be folded into a convenient size to carry in a health care practitioner's pocket, wallet, or purse, and the probe may be protected within the folding card when the folding card is folded in a certain position.

12 Claims, 3 Drawing Sheets

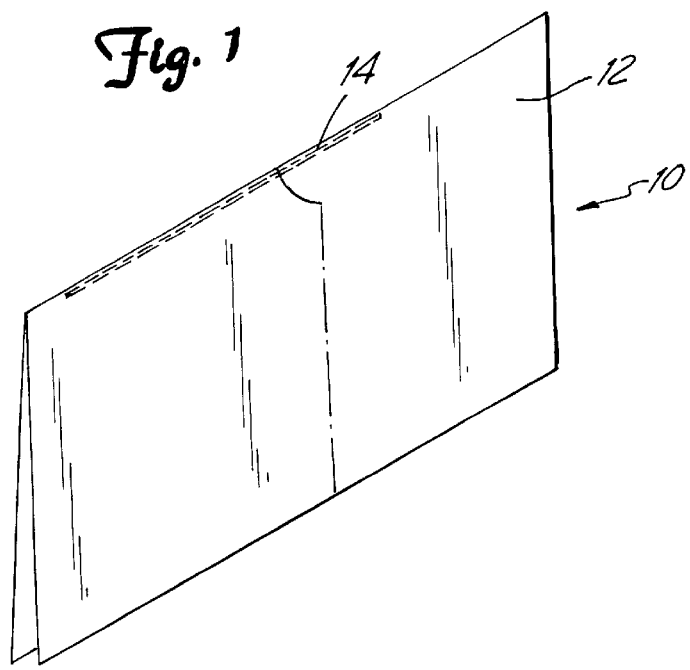
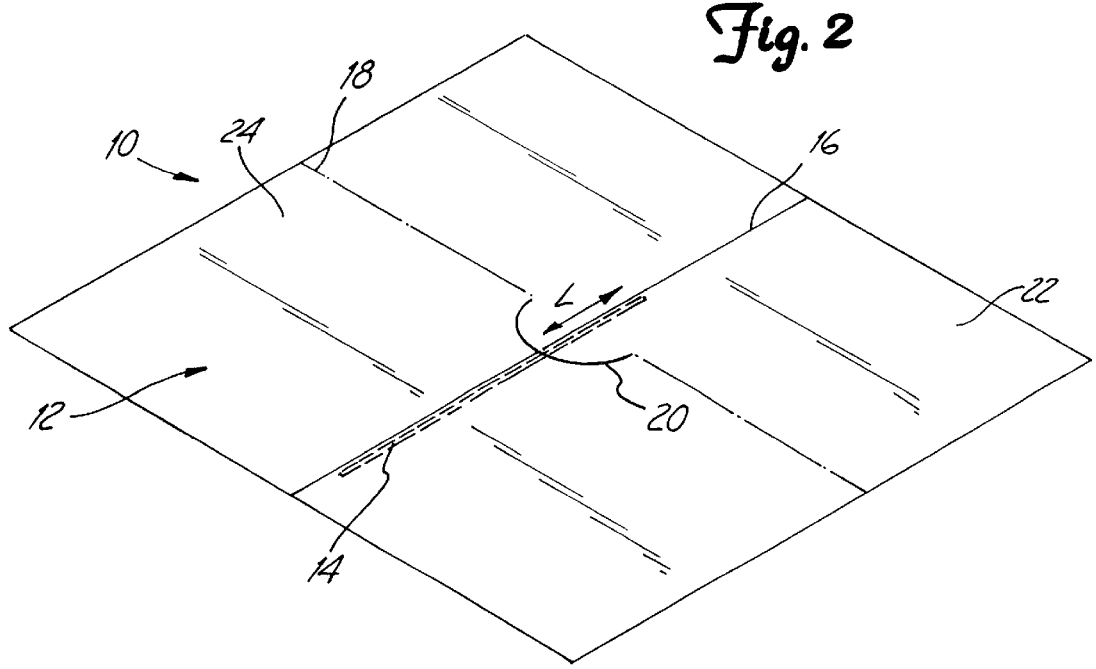

FOLDING CARD DEVICE FOR EVALUATING PROTECTIVE SENSATION

FIELD OF THE INVENTION

The present invention relates to a device used by health care providers for detecting a patient's loss of protective sensation. More particularly, it relates to an improved monofilament-type device used for this purpose.

BACKGROUND OF THE INVENTION

Protective sensation, or ability to feel pain, is the body's warning system that enables an individual to avoid injury and that alerts the individual when injury does occur. Certain neurological and other medical examinations require the detection of impaired or lost sensitivity. Such detection is particularly important for patients with certain diseases or disabilities. For example, nearly half of all diabetes patients in the United States develop diabetic neuropathy, a complication that suppresses a patient's ability to feel pain. Diabetic peripheral neuropathy is characterized by loss of protective sensation, which may be manifested as analgesia (absence of pain or touch sensitivity), hyposthesia (reduced sensitivity), weakness, or autonomic changes. Loss of protective sensation is that degree of sensory loss that permits cutaneous injury to occur without being perceived by the patient as painful.

When due to neuropathy, loss of protective sensation is a major permissive factor in the pathogenesis of foot injury, and often leads to ulceration, infection, and, potentially, amputation. These problems are significant: Approximately 15% of diabetes patients sustain foot or leg ulcers, and may reacquire them in the absence of preventive and protective intervention. In addition, diabetic foot ulcers account for more than 20% of total hospital days for patients with diabetes, and they are the leading cause of hospital admissions for diabetic patients. Approximately 50% of all nontraumatic amputations in the United States are caused by complications from diabetes.

Routine testing for loss of protective sensation is critical, particularly for at-risk patients, such as those with diabetes. Prior art devices, however, are cumbersome and relatively expensive, and thus hinder such routine testing. For example, the device disclosed by Low et. al, U.S. Pat. No. 3,662,744, issued May 16, 1972, telescopically extends and retracts a monofilament. This device requires the health care practitioner to turn a knob to extend the monofilament each time the device is used, to ensure the proper length of monofilament is extended from the device, and to turn the knob to retract the monofilament when done. Because the length of monofilament extended from the device is variable, the health care practitioner has difficulty knowing how much force is being exerted by the monofilament on the patient. The device also has many moving parts, and thus is relatively costly to manufacture.

The Semmes-Weinstein esthesiometer, which currently is in widespread use, also has disadvantages. The Semmes-Weinstein device consists of a monofilament that is permanently attached at a 90 degree angle to the end of a plastic rod. The monofilament is always exposed, and thus is prone to damage. To compensate, the device generally is kept in a protective case in a drawer. The result is that the device is often not conveniently accessible to the health care provider, and thus is not used on a consistent basis.

Other devices solve some of the problems of the prior art by protecting the monofilament from damage, but these devices are somewhat bulky and are therefore more difficult than necessary for a health care practitioner to carry. One device, disclosed in Applicant's application Ser. No. 08/719,167, discloses a device wherein the probe is protected within a handle member when not in use.

There is need for a device for evaluating protective sensation that is convenient to carry and easy to operate, thereby enabling health care practitioners to evaluate routinely whether their patients have lost protective sensation. Such a device preferably also will be inexpensive, small, lightweight, and sized to fit within a health care practitioner's pocket.

SUMMARY OF THE INVENTION

In one embodiment, the invention is a device for evaluating protective sensation, comprising a probe and a folding card attached to the probe, such that a portion of the probe extends from the folding card when the folding card is in a first position. In this embodiment, the folding card may be folded such that the probe is enclosed by and protected by the folding card. This embodiment may be advantageous in that the probe may be protected by the folding card and hence out of harm's way when the folding card is folded to enclose the probe.

Another embodiment of the invention is a device for testing protective sensation of a patient's skin, comprising a monofilament probe and a folding card attached to the monofilament probe adjacent a first crease, wherein the monofilament probe extends outwardly from the folding card when the folding card is folded in a first position, and the monofilament probe is enclosed and protected by the folding card when the folding card is folded along the first crease in a second position. Much like the previous embodiment, the folding card may be folded in a position such that the monofilament probe is protected by the folding card, such that it will not be damaged easily.

Each of the embodiments described above offer the advantage of providing a lightweight device that may be carried easily by a health care practitioner to measure the protective sensation of a patient's skin. The device may easily fit into a health care practitioner's pocket, wallet, or purse, and in one embodiment the folding card may be folded into a card the size of a typical business card. Each embodiment also offers the advantage of folding into a form that protects the probe when the device is not in use.

These and other objects and advantages of the present invention will become apparent with reference to the drawings, the description of the preferred embodiment, and the appended claims.

BRIEF DESCRIPTION OF THE DRAWINGS

FIG. 1 is a perspective view of the present invention in its closed state.

FIG. 2 is a top view of the present invention in its open state.

DETAILED DESCRIPTION OF THE INVENTION

FIG. 1 depicts the sensitivity-testing device 10 of the present invention in a closed state. The device 10 comprises a folding card 12 and a probe 14. The folding card 12 may be made from a wide variety of generally rigid or partially rigid sheet materials, such as paper, cardboard, heavy paper such as that used for business cards, or plastic. When in the folded and closed position of FIG. 1, the folding card 12 may, in one embodiment, be approximately the size of a standard business card, which is approximately 3½ inches by 2 inches. In the unfolded position, as seen in FIG. 2, the folding card may be approximately 3½ inches by 4 inches. In other embodiments, however, the size of the folding card 12 can vary. The folding card 12 may be a single, continuous piece, or multiple pieces attached together at joints. The term "folding card" will be used throughout this specification to refer to a card as described above which is capable of being easily folded into at least two positions. A substantial amount of information, such as instructions or advertising information, including physician or clinic names and addresses, may be printed on the folding card 12. The device 10 may therefore be used for advertising purposes.

Figure 3:
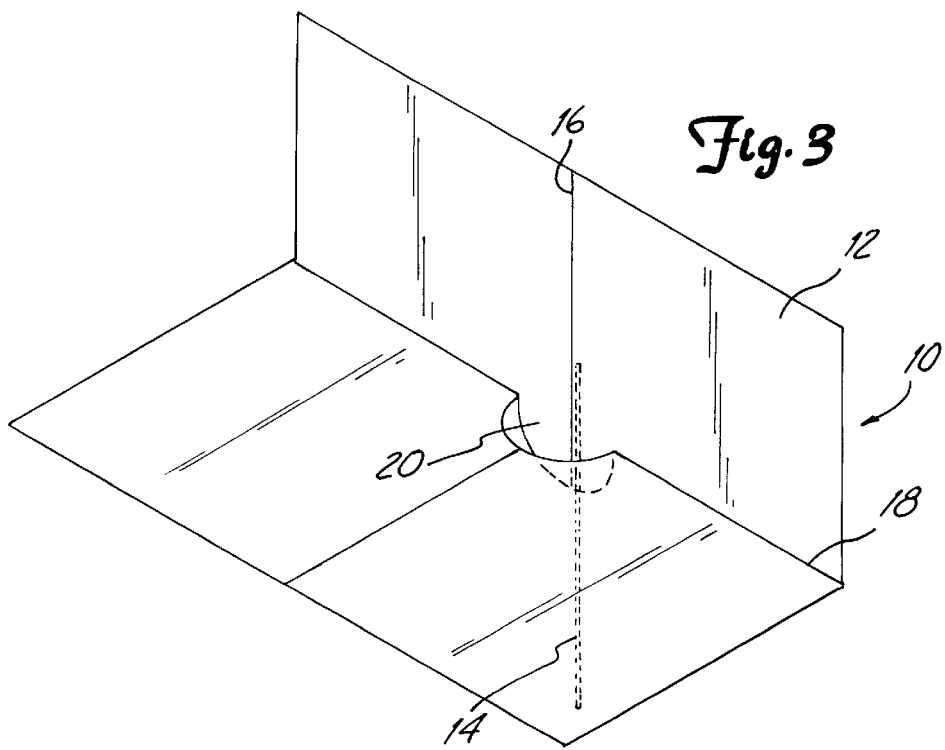
FIG. 3 is a view of the present invention in a partially folded state in preparation for use.
Figure 4:
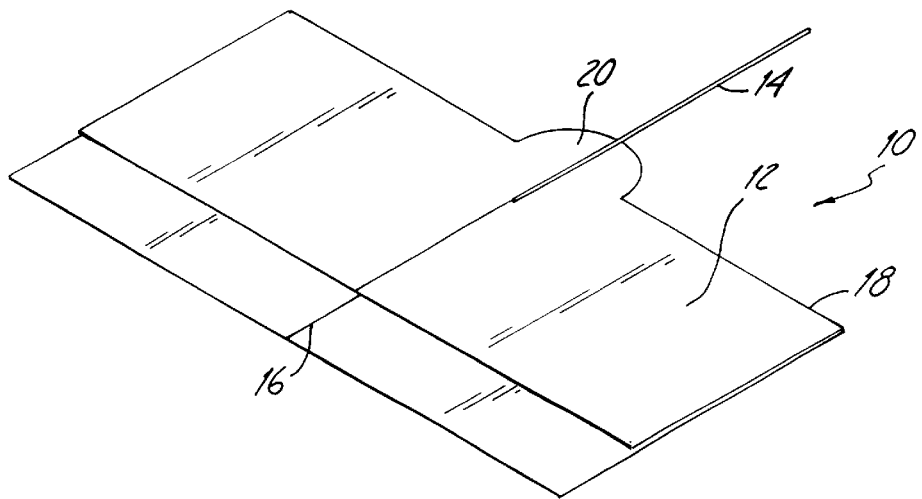
FIG. 4 is a second view of the present invention in a further partially folded state in preparation for use.
Figure 5:
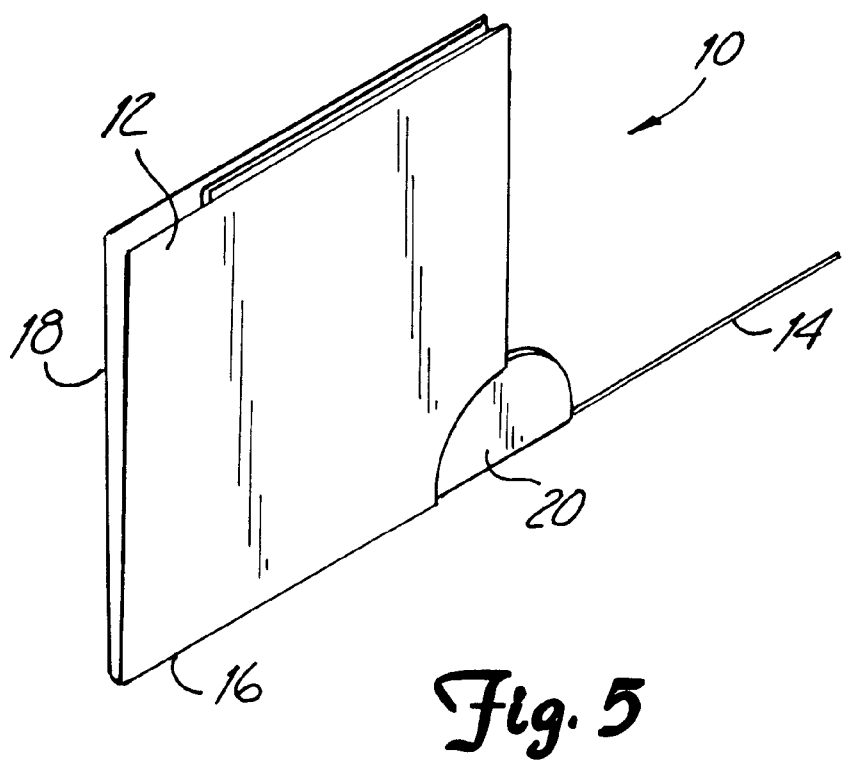
FIG. 5 is a view of the present invention in a fully folded state in preparation for use.

Attached to the folding card 12 is a probe 14, which is shown in phantom in FIGS. 1–3 and more clearly in FIGS. 4 and 5. The probe 14 may be attached to the folding card 12 adjacent or on a first crease 16 in the fold card 12. The first crease 16 may separate the folding card into two portions 22, 24. The probe 14 may be attached to either portion 22, 24 (portion 22 in FIG. 2) near the first crease 16, or the probe 14 may be attached to the first crease 16 itself.

In one embodiment, the probe 14 is a monofilament that is relatively stiff but flexible. In this embodiment, the monofilament may be generally cylindrically shaped, approximately 30–70 millimeters in length, more particularly 47.5 millimeters in length, and approximately 0.017 inches in diameter. The monofilament used in the present invention may be made of a polymeric material such as nylon. One suitable monofilament that may be used with the present invention has a filament index number of 5.07, and is available as Nylon 612. In use, a probe 14 of the preferred type applies a force to the patient's skin of 10 grams; when more than 10 grams of force is applied by the health care practitioner, the probe 14 bends, and eventually will slip off the user's skin or kink. By using a thicker or shorter probe 14, the device 10 can be made to exert greater force on the patient's skin. Conversely, when a thinner or longer probe 14 is used, the device 10 will exert less force on the patient's skin.

The probe 14 may be attached to the folding card 12 along the first crease or score 16, and more particularly along the first crease 16 for a certain distance leading up to a cutaway 20 or second crease 18, which may be generally perpendicular to the first crease 16. The cutaway 20 may be used in one embodiment to act as an adhesive boundary and serve as an extended holder for the probe 14. This cutaway 20, therefore, made aid in the stability of the probe 14 when the probe 14 is in the extended position from the folding card 12, as depicted in FIGS. 3–5. In the embodiment shown in FIGS. 1–5, in which the folding card 10 is generally rectangular in shape when unfolded (as in FIG. 2), the first crease 16 may run across the short length of the folding card 12 approximately midway along the longer length of the folding card 12. In this embodiment, the second crease 18 may run across the longer length of the folding card 12 approximately midway along the short length of the folding card 10. The locations of the first crease 16 and second crease 18 may, however, vary, such that they need not be located at a midpoint along a length of the folding card 12. The probe 14 may also be attached along either the first crease 16 or the second crease 18. The first crease 16 may also be referred to as the main crease, because, as seen in FIG. 1, the folding card 12 may fold along the main crease to enclose and protect the probe 14 when the device 10 is not in use.

The use of the phrases "first crease" and "second crease" in this specification is not meant to limit the scope of the invention. The first crease 16 and second crease 18 may be simple creases, folds, or scores in the folding card 12 which are reinforced with tape, or the first crease 16 and second crease 18 may be perforations that are bound with tape to keep the folding card 12 together. The creases 16, 18 and other perforations may be cut or scored into the folding card 12 in any method known to those skilled in the art, including the use of standard cutting dies, razor blades, or the like.

In the embodiment shown in FIG. 2, the probe 14 is attached to the folding card 12 adjacent the first crease 16 for a length L. This length L may vary, such that the remaining portion of the probe extending past the length L may also be altered. As noted above, a shorter probe 14 may be used to apply a greater force to the patient's skin. In one embodiment, the remaining portion of the probe 14 extending past the length L may be approximately 30–50 millimeters, and more particularly 38 millimeters. The selection of this remaining, extending portion of approximately 38 millimeters may yield 10 grams or less of force on the patient's skin when the probe 14 buckles, and thus the selection of this extending portion may, in one embodiment, be important for this reason. The selection or attachment of a probe 14 with an extending portion (beyond the length L) of approximately 38 millimeters may be appropriate to yield a force of 10 grams or less with a monofilament having a filament index number of 5.07, such as a Nylon 612 monofilament. FIG. 2 depicts a semi-circular perforation 20 (also referred to as a cutaway 20 above), which is formed along and associated with the second crease 18 and intersects the first crease 16 at a right angle. In one embodiment, the probe 14 may be attached along the length L up to the perforation 20, as can be clearly seen in FIGS. 3–5. The remaining portion of the probe 14 may then extend from the folding card 12 when in use, as can also be seen in FIGS. 3–5. In another embodiment, the perforation 20 need not be formed in the folding card 12. Instead, the probe 14 may simply be attached along length L until the first crease 16 intersects the second crease 18.

The probe 14 may be attached to the folding card 12 in a variety of means known to those skilled in the art. In one embodiment, a hot melt adhesive may be used to attach the probe 14 to the folding card 12. In this embodiment, the probe 14 may be dipped into a hot melt adhesive, the excess adhesive may be wiped from the probe 14, and then the probe 14 may be attached to the folding card 12. In another embodiment, a heat staking method may be used to attach the probe 14 to the folding card 12. The probe 14 may also be attached to the folding card 12 using tape, any form of adhesive, glue, or bonding, or any other method known to those skilled in the art.

FIG. 1 illustrates the testing device 10 wherein the folding card 12 is in the folded position such that the probe 14 is protected. In this position, the device 10 may be carried in a pocket, wallet, or purse of a health care practitioner and may be ready for use without any assembly. In this embodiment, the device 10 should be lightweight and easy to carry. Its nature also is concealed from the patient, who will then have no preconceived notions about the sensation he or she soon may feel. This helps ensure an unbiased response.

The use of the present invention now will be described. FIGS. 3–5 illustrate the orientation of the device 10 when in use. FIG. 3 shows the extension of the probe 14 from the folding card 12 when the folding card 12 is folded along the second crease 18, such that the free end of the probe 14 rotates away from the surface of the folding card 12. FIG. 4 shows the folding card 12 folded completely (180 degrees) over the second crease 18. FIG. 5 shows the folding card 12 folded once more, along the first crease 16. In the orientation of either FIG. 3, 4, or 5, the health care practitioner can grip the folding card 12 with the probe 14 extending, such that the probe 14 may be used in skin sensitivity testing. The folding card 12 length from the extended probe 14 to the end of the folding card 12 held by the health care practitioner may act to distance the health care practitioner's fingers from the patient's tissue being tested.

In use, the folding card 12 is folded as in FIG. 3, 4, or 5, and the probe 14 is applied perpendicular to the patient's skin, out of the patient's sight. The health care practitioner may apply enough force to the folding card 12, and thereby against the patient's skin, to bend the probe 14 for approximately 1.5 seconds. When a force is applied against the patient's skin, the probe 14 will bend. Patients who cannot feel the kind of pressure applied by the device 10 may have lost protective sensation, and may be at increased risk for injuries that may lead to neuropathic ulcers. Upon detection of a patient's loss of protective sensation, proper medical treatment may be prescribed. After using the device 10, the health care practitioner may discard the device 10 or clean the probe 14 by wiping it with alcohol or by washing it with detergent and water. Because the materials of the device 10 may be cheap, the device 10 may be disposable in one embodiment. The device 10 may then be closed by folding the folding card 12 into the position shown in FIG. 1.

Although the description of the preferred embodiment has been presented, it is contemplated that various changes may be made without deviating from the spirit and scope of the present invention. Accordingly, it is intended that the scope of the present invention not be limited strictly to that of the above description of the present invention.

I claim:

1. A device for evaluating protective sensation, comprising:
   (a) a probe; and
   (b) a folding card attached to the probe, wherein the folding card contains a crease system having first and second creases for folding, with the second crease being substantially perpendicular to the first crease such that a portion of the probe extends from the folding card when the folding card is in a first position so that the probe may be used to evaluate protective sensation, and wherein and the probe is enclosed and protected by the folding card when the folding card is in a second position.

2. The device of claim 1, wherein the probe is a monofilament.

3. The device of claim 2, wherein the probe is polymeric.

4. The device of claim 1, wherein the probe is attached to the folding card with an adhesive.

5. The device of claim 1, wherein the folding card is the size of a business card when folded.

6. The device of claim 1, wherein the probe is attached to the folding card for a length L substantially along the first crease up to the second crease.

7. The device of claim 1, wherein the folding card contains a semi-circular perforation associated with the second crease from which the probe extends.

8. The device of claim 7, wherein only a portion of the probe is attached to the folding card.

9. A device for testing protective sensation of a patient's skin, comprising:
   (a) a monofilament probe; and
   (b) a folding card attached to the monofilament probe adjacent first crease, wherein the monofilament probe extends outwardly from the folding card when the folding card is folded in a first position so that the probe may be used to evaluate protective sensation, and the monofilament probe is enclosed and protected by the folding card when the folding card is folded along the first crease in a second position.

10. The device of claim 9, wherein the folding card may be the size of a standard business card when folded in the second position.

11. The device of claim 9, wherein the folding card contains a perforation along the second crease, and wherein the monofilament probe is attached to the folding card for a length L adjacent the first crease up to the perforation.

12. A device for testing protective sensation of a patient's skin, comprising:
   (a) a monofilament probe; and
   (b) a folding card, wherein the monofilament probe is attached to the folding card with an adhesive for a length L adjacent a first crease in the folding card up to a second crease in the folding card, wherein the second crease is substantially perpendicular to the first crease, and wherein the monofilament probe extends outwardly from the folding card when the folding card is folded in a first position, and wherein the monofilament probe is enclosed and protected by the folding card when the folding card is folded along the first crease in a second position such that the folding card is substantially the size of a standard business card.

* * * * *

UNITED STATES PATENT AND TRADEMARK OFFICE
CERTIFICATE OF CORRECTION

PATENT NO.    : 6,200,272 B1
DATED         : March 13, 2001
INVENTOR(S)   : Harry Linden It is certified that error appears in the above-identified patent and that said Letters Patent is hereby corrected as shown below:

<u>Column 6,</u>
Line 20, "a folding card attached", should read -- a folding card having first and second creases for folding, with a second crease being substantially perpendicular to the first crease, said card being attached --.

Signed and Sealed this

Seventeenth Day of January, 2006

JON W. DUDAS
*Director of the United States Patent and Trademark Office*